(12) United States Patent
Voon et al.

(10) Patent No.: US 6,990,845 B2
(45) Date of Patent: Jan. 31, 2006

(54) PENDULUM IMPACT TEST RIG

(75) Inventors: Wong Shaw Voon, Seri Kembangan (MY); Radin Umar Radin Sohadi, Kajang (MY); Abdel Magid S. Hamouda, Kuala Lumpur (MY); Megat Mohamad Hamden Megat Ahmad, Kajang (MY); Tan Kean Sheng, Georgetown (MY)

(73) Assignee: Universiti Putra Malaysia, Selangor (MY)

( * ) Notice: Subject to any disclaimer, the term of this patent is extended or adjusted under 35 U.S.C. 154(b) by 166 days.

(21) Appl. No.: 10/713,018

(22) Filed: Nov. 17, 2003

(65) Prior Publication Data
US 2004/0103713 A1   Jun. 3, 2004

(30) Foreign Application Priority Data
Nov. 18, 2002   (MY) .................................... P120024307

(51) Int. Cl.
*G01N 3/00* (2006.01)

(52) U.S. Cl. ..................................................... 73/12.14
(58) Field of Classification Search ............... 73/12.21, 73/12.14, 12.09
See application file for complete search history.

(56) References Cited

U.S. PATENT DOCUMENTS

| | | | | |
|---|---|---|---|---|
| 4,425,786 A | * | 1/1984 | Sirkkola et al. | ........... 73/12.14 |
| 5,003,811 A | * | 4/1991 | Shannon et al. | ........... 73/12.14 |
| 5,922,937 A | * | 7/1999 | Kowalski et al. | ........... 73/12.14 |
| 6,505,498 B2 | * | 1/2003 | Pringle | ....................... 73/12.04 |

* cited by examiner

*Primary Examiner*—Max Noori
*Assistant Examiner*—Corey D. Mack
(74) *Attorney, Agent, or Firm*—Bacon & Thomas, PLLC

(57) ABSTRACT

The pendulum impact test rig is designed and developed for simulating impact conditions experienced by structural components in real-world crash or full-scale crash test. The test rig can be adopted for crash testing individual vehicle component. The test rig comprises of a base plate which is anchored to a concrete ground, a pendulum supporting structure positioned on the base plate, a pendulum member constructed from structural T-beam that permanently secured to a rotatably shaft, and a test item holding device releasably mounted on the base plate. The pendulum member includes a striker which is releasably attached to the lower end portion of the pendulum, fixed masses permanently secured at the lower end portion of the pendulum, and additional masses detachably attached immediately above the fixed masses. With present preferred embodiment, the center of percussion is controlled within the striking zone. Computer-based instrumentation system, which comprises accelerometer, high speed imaging system, light beam emitter-detector velocity measurement, data acquisition card, and computer with data acquisition and analysis application software installed is provided so that the desired data can be acquired for analysis and presentation.

17 Claims, 5 Drawing Sheets

PENDULUM IMPACT TEST RIG

FIELD OF INVENTION

The present invention relates generally to a crash testing rig for structural component, and more specifically to a heavy-duty crash testing rig designed for simulating crash conditions during frontal direct crash for motorcycle frontal components and for impact tests on other vehicle components.

BACKGROUND OF THE INVENTION

There is an increasing interest in investigating the dynamic strength and impact characteristics of various vehicle components in the effort to enhance the crashworthiness features of those components. Actual full-scale crash tests to assess crashworthiness of vehicle components such as motorcycle or automobile wheels is expensive and space consuming since they require the use of sleds or moving barriers to simulate the impact. This is particularly inappropriate and unworthy when only a specific critical component of a vehicle is to be investigated, under varying impact conditions and great number of test parameters. In such a case, a laboratory component testing would be a better approach. It is to be emphasized that the laboratory impact simulation tests can never exactly duplicate the real-world impact conditions. However, it is important that any laboratory component impact test system is at least capable to simulate the essential and critical characteristics of impact experienced by structures in real-world conditions.

There are many different techniques for such low velocity but relatively high load simulation crash testing, in terms of propulsion being utilized to operate the impact test system such as gravity force, mechanical ram, explosive guns, etc. The gravity propelled type is the most commonly employed since a large percentages of crashworthiness studies lie within the limits of medium strain rate regime, with strain rate range from $0.1s^{-1}$ to $200s^{-1}$, which is within the capability of gravity propelled test system. The gravity propelled type also offers a cost effective advantage. Two types of gravity propelled impact machines are the drop weight and pendulum types. Such test systems are usually readily available from specialized suppliers with their performance and quality guaranteed. Among the shortcomings of such test system are expensive and may not suit the requirement of testing, the working space may be limited to a small test specimen. In contrast, when a pendulum or drop weight test rig is required by a laboratory, most of the laboratories will opt to carry out the design, development and calibration of the system in-house. This is because it is more economical and can be made to a desired degree of flexibility, working space and rigidity. This is especially true for development of heavy-duty special purpose impact test system. The major drawback of in-house fabrication is that expertise is highly needed in mechanical and electronic installation and commissioning to ensure a reliable performance.

However, pendulum type impact test rig offers several advantages compared to drop weight type. For a given drop height the pendulum will give the highest impact velocity providing the mass distribution is not biased heavily towards the fulcrum. Also, for the same drop height, the pendulum striker travels considerably farther and has almost constant velocity when it impacts the test item. Free-fall carriages have to be guided and thus the friction can vary not only due to binding during the actual free fall but also due to more severe binding after the striker hits the test item and creates some offset loading. Providing the pendulum uses ball bearings, the friction is negligible and constant throughout its travel. The relatively high friction of drop weight type striker also contributes to the lower velocity that can be achieved at similar falling height compared to pendulum type. A simple pendulum type impact test rig is simple to construct and can be accommodated easily in most commercial buildings with reasonable ceiling height. The free fall test rig requires expensive and rigid guidance equipment if binding is to be kept to a minimum. In terms of maintenance, a pendulum with just two self-aligning bearings is easy to maintain whereas free fall equipment with its guides and linear bearings is difficult to maintain.

One known heavy-duty pendulum impact test rig is that which developed for SAE J1981 standard for automobile wheel-tyre assemblies road hazard impact test. Test item is attached to a holding fixture which constructed of tubular upright part and cantilevered horizontal part. The test rig is capable of generating the rated maximum impact velocity of about 33 km/h and the maximum impact energy of about 1.6 kJ, corresponding to the maximum impact velocity. One of the disadvantages of this test rig is its relatively high deviation of center of percussion from the striker nose, or the impact region. Difficulties that would occur with this are:

(1) Shock will be transmitted back to the supporting frame, and this would causes erroneous readings of the impact value.

(2) The pendulum will be more susceptible to damage by bending or by fracture.

(3) The pendulum will absorb high deformation energy causing erroneous impact readings.

(4) The bearings will deteriorate rapidly.

Another disadvantage is that the test rig does not provide flexibility for varying the striking weight. This characteristic is favourable to allow varying impulsive forces to be applied on the test component.

In another prior art light-duty pendulum impact test rig, the pendulum arm is constructed to extended above its pivot point by an amount equal to one-half of the stem length suspended below the pivot point so that the center of percussion will be located exactly at the center of the striking edge. In such condition, the pendulum portion that extended above the pivot point would become longer as the length suspended below the pivot point increases. The problem with this is it creates a laterally instability when the pendulum swings, which will cause a connection failure at pivot point and deteriorate the bearings that support the shaft. Also, it creates a significant moment at the extended portion that oppose to the striking moment which will reduce the effective velocity, force, and energy delivered.

Accordingly, the principal object of the present invention is to provide an economic yet reliable tool for performing frontal direct crash tests on motorcycle frontal components and impact tests for other vehicle components, which utilizes a large pendulum structure for generating the impact energy and impact velocity required. The further object of the present invention is to provide a impact test rig for crash testing other structural components. Another object of the invention is to developed a pendulum hammer with its center of percussion controllable in the vicinity of the striking region whilst allow for varying the striker location and striking weight. It is desirable to provide an impact test rig with large working space which would be able for placing a large structural test item such as a complete motorcycle. It is desirable to provide such a test rig which able to simulate critical characteristics of impact in real-world and full-scale crash test conditions.

SUMMARY OF THE INVENTION

According to the present invention, a pendulum impact test rig comprises a base plate, a pendulum supporting structure positioned thereabove, a pendulum member constructed from structural T-beam that permanently secured to a rotatably shaft, and a test item holding device releasably mounted on the base plate. The pendulum member includes a striker which is releasably attached to the lower end portion of the pendulum, fixed masses permanently secured at the lower end portion of the pendulum, and additional masses detachably attached immediately above the fixed masses. Spherical roller bearings are selected to give maximum support to the shaft while allow for misalignment that may occur from shaft mounting errors or shaft deflections during operation.

In the present invention, the following fundamental design criteria of the pendulum have been established:

(1) The arm should have sufficient length in order to achieve the targeted impact energy and impact velocity.

(2) The arm needs to be fabricated using steel for long service life, rather than other lightweight materials that would be less robust.

(3) The arm carries high torsional rigidity sufficiently to resist twisting moment upon impact.

(4) The inertia and mass of the pendulum have to be as low as possible.

(5) The center of percussion of the pendulum needs to be as close as possible to the impact line, in order to minimize the impulsive reaction that may cause the deformation and bending of the arm, and eventually the whole system.

(6) Ease of installation.

(7) Reliable and convenient arm lifting and quick releasing mechanisms.

(8) High repeatability and reliability.

According to the present invention, the most important feature of the pendulum test rig is that it allows for controllable center of percussion in the impact region while allow for varying the striking weight and varying the locations of striker along the lower end portion of the pendulum arm. The present pendulum test rig is found to have a better controlling feature of center of percussion of the pendulum compared to that developed for SAE J1981 standard. With equivalent arrangement, the percentage of deviation of center of percussion from midpoint of striker's striking edge is found to be about 14% for the pendulum developed for SAE J1981 but is about only 7% for the present developed pendulum. A structural T-beam is selected as pendulum arm instead of other types of structural beam in the present invention for several reasons. Firstly is that the T-beam reduces a weight of the arm to a large extent compared to other types of beam such as square type and I-beam for equivalent length. This is helpful for controlling the center of percussion in the lower end portion of the arm, where the striker is usually located or the impact always occurs. Secondly is that the space behind the flange and at both sides of the web provides a suitable place to locate the fixed masses and a series of additional masses, where the web is used to secure these masses whereas the flange gives a front support when the pendulum swing and impact the test specimen. The fixed masses assist to locate the center of percussion in the striking region. The series of additional masses varies the striking weights that can be applied and to generate a higher impact energy. In a preferred embodiment, the pendulum arm is constructed in such a way that it can be raised to about 170° from free hanging position in order to optimized its capacity In a preferred embodiment, a striker is releasably, rather than permanently, secured to the arm. This is to facilitate the removal of the striker for replacement when damage, for shifting to a lower or higher location along the end portion of the arm for impacting with test item at different location, and for exchanging different designs of striker to better simulate the impact conditions experienced by the test body resulted from different striking object with different geometry of contact surface.

A pendulum arm hoisting and quick releasing mechanism comprised of drive shaft, mechanical drive, gear box and pulley system. Clutch coupling mechanism is employed between the pendulum mounted shaft and drive shaft for maintaining the pendulum arms in its ready position and enabling the quick releasing of the pendulum. When the clutch coupling means is manually actuated, the pendulum swings downwardly and impacts the test body and fractures the test body.

Computer-based instrumentation system is provided so that the desired data can be acquired for analysis and presentation. The system comprises accelerometer, high speed imaging system, light beam emitter-detector velocity measurement, data acquisition card, and computer with data acquisition and analysis application software.

DETAILED DESCRIPTION OF THE INVENTION

Figure 1:
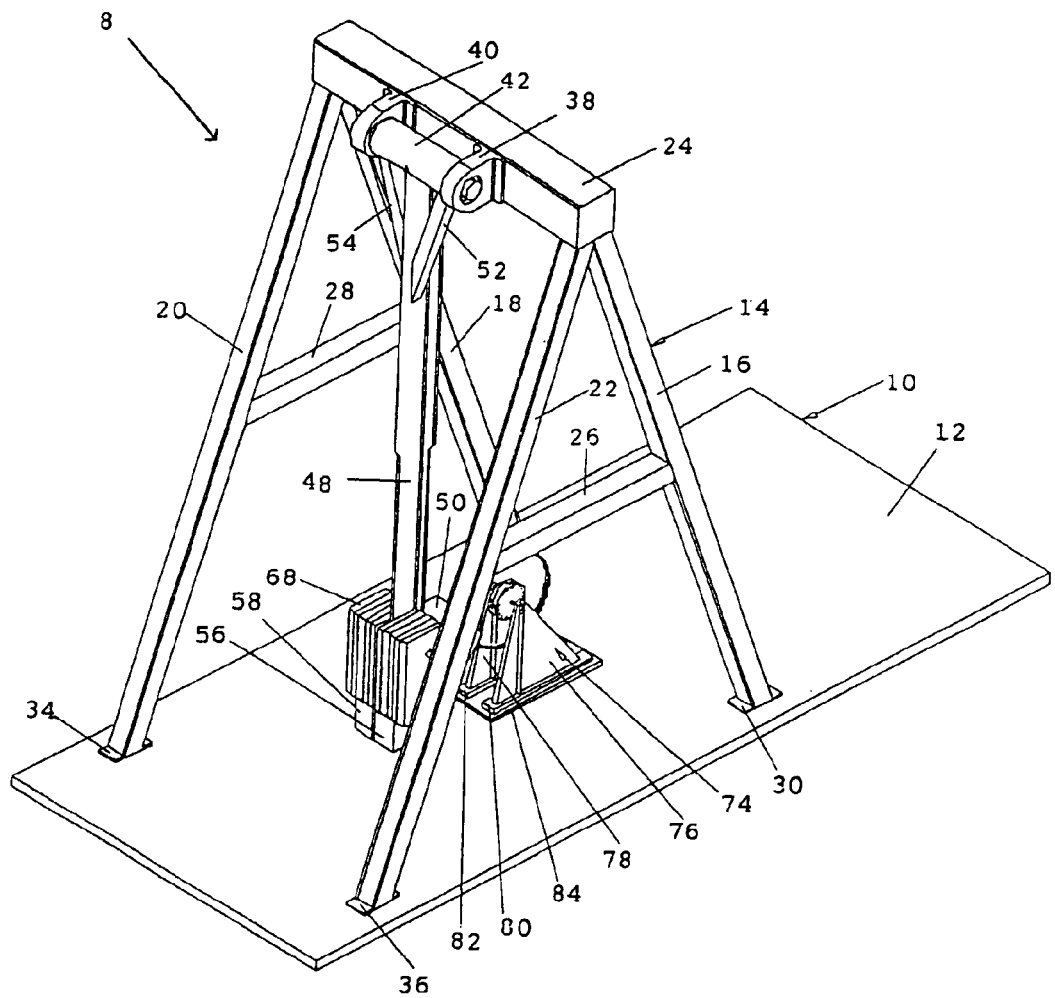
FIG. 1 is an isometric view of an impact test rig in accordance with the present invention.
Figure 2:
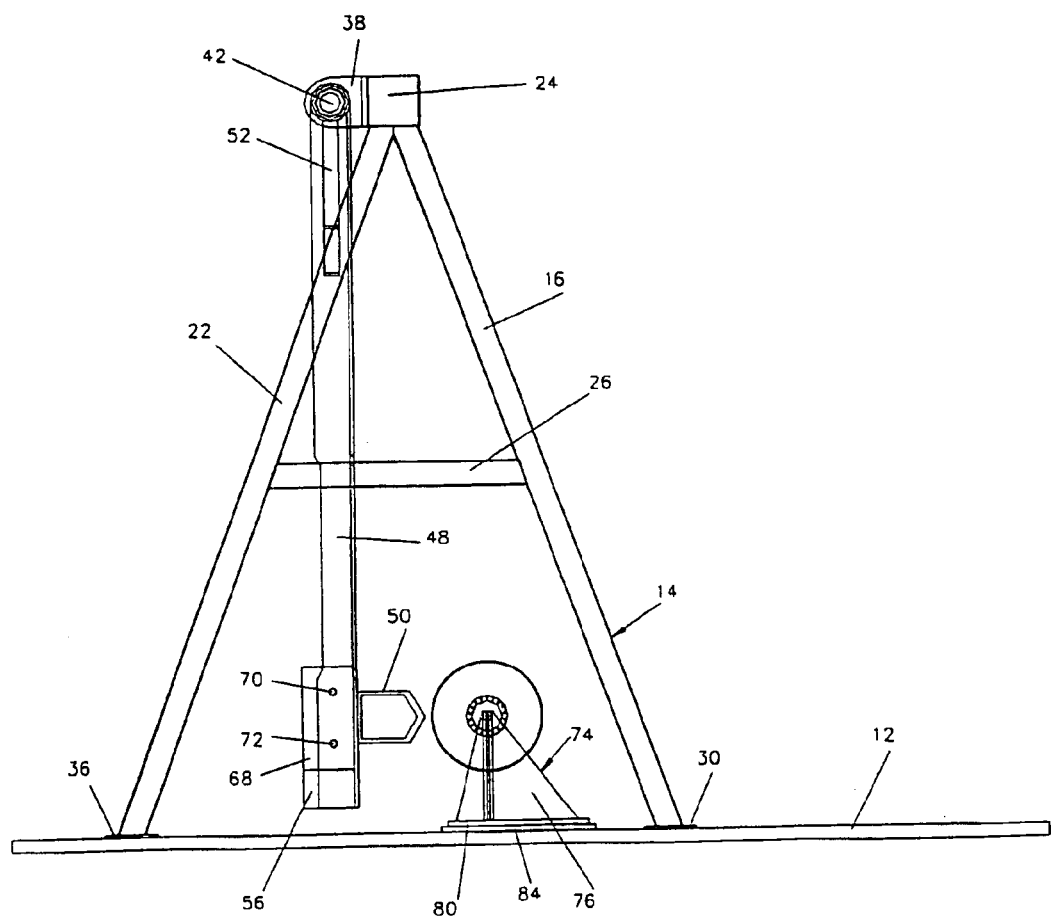
FIG. 2 is a front view of the impact test rig shown in FIG. 1.
Figure 3:
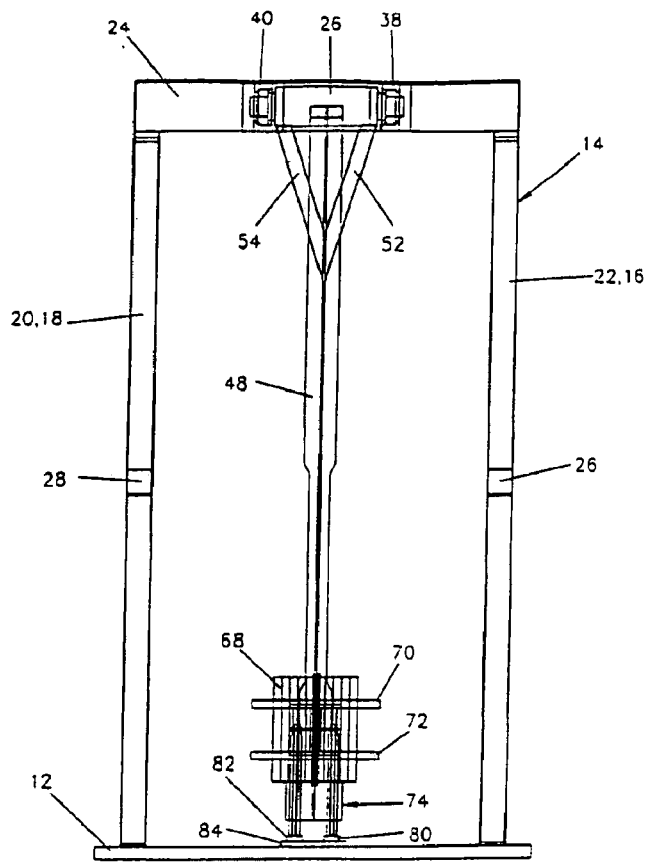
FIG. 3 is a side view of the impact test rig shown in FIG. 1.

FIGS. 1 to 3 illustrates a pendulum impact test rig (8) according to the preferred embodiment of the present invention for crash testing the structural components. The test rig (8) is generally comprises of base portion (10) and pendulum supporting frame (14) positioned thereon.

In a preferred embodiment, base portion (10) is generally a thick plate member (12), which is preferably secured to a suitable supporting surface such as a concrete floor or the like by any convenient means such as bolts. The pendulum supporting frame (14) is a pair of "A" structure supporting frames, constituted of four inclined upstanding structural frame members (16, 18, 20, 22), one horizontal main frame member (24) secured to the vertex of the upstanding structural frame members (16, 18, 20, 22) and another two horizontal structural frame members (26, 28) which are secured to and extend between the frame members (16, 22) and (18, 20) respectively for extra support. At the bottom of the upstanding structural frame members (16, 18, 20, 22) are small plates (30, 32, 34, 36) which are used to secure the pendulum supporting frame (14) to the thick plate member (12). These small plates (30, 32, 34, 36) are bolted to the ground through the thick plate member (12).

Horizontal main frame member (24) provides a mountable structure for mounting the brackets (38, 40) that hold the shaft (42). These brackets (38, 40) are bolted to the horizontal main frame member (24) and provide housing for the spherical roller bearings. Both ends of the shaft (42) are press fit into the bearings. A pendulum arm (48) is suspended from the shaft (42) with its upper end securely welded to the said shaft (42) and a striker (50) releasably secured to its lower end. The pendulum arm (48) is preferably constructed of a structural T-beam. Two inclined frame members (52, 54) are welded at one of their end to both left and right sides of the pendulum arm (48) whilst the other end are securely welded to the shaft (42). Fixed masses (56, 58) preferably fabricated from high density material such as steel box filled with lead, are securely welded to the end of the pendulum arm (48).

Any of convenient and reliable arm lifting and quick releasing can be employed for the present invention. In a preferred embodiment, the shaft (42) is driven by reversible drive shaft through clutch coupling to aid in hoisting and quick releasing mechanism of the pendulum arm (48). The drive shaft is connected to a simple manual pulley via mechanical drive such as belt or chain drive and gear box (not shown). Pulley acts as a hoisting mean whereas the gear box reduces the torque required to operate the pulley. The pulley can be operated by simply pulling the chain, one is to lower the pendulum arm (48) and the other one is to raise the pendulum arm (48). The coupling between shaft (42) and drive shaft enables the shaft (42) to be rotated together with drive shaft when pulley is operated and thus raise the pendulum arm (48). The connection of the clutch coupling also enables the pendulum arm (48) to be held at a selected height, or a ready position before it is released. The pendulum arm (48) can be immediately released upon uncoupling the drive shaft from shaft (42) by pulling the drive shaft away from coupling surface with said shaft (42).

Figure 4:
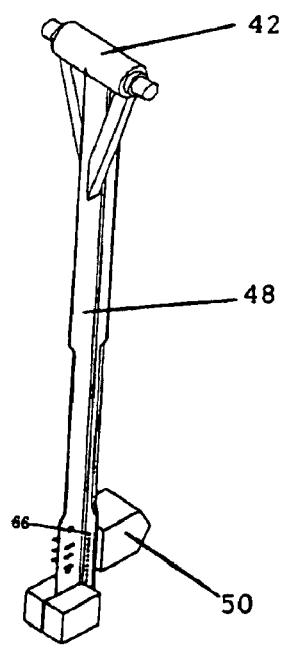
FIG. 4 illustrates the assembly of the pendulum arm attached with different type of striker.
Figure 5:
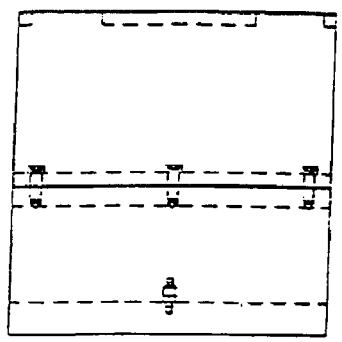
FIG. 5 illustrates the details of the strikers and accelerometer mounting location for triangular type striker.
Figure 5:
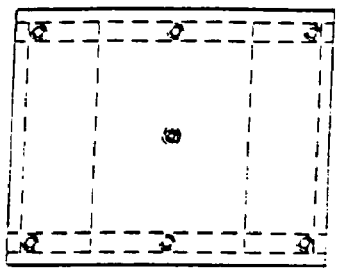
Figure 5:
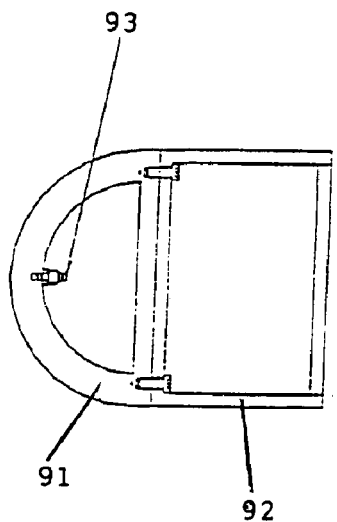
Figure 6:
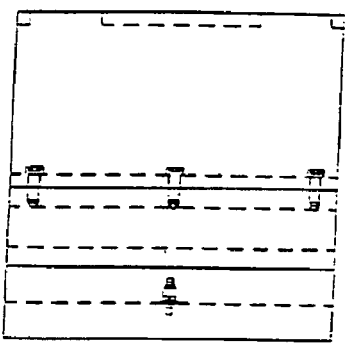
FIG. 6 illustrates the details of the strikers and accelerometer mounting location for hemispherical type striker.
Figure 6:
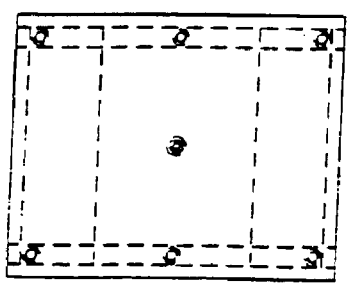
Figure 6:
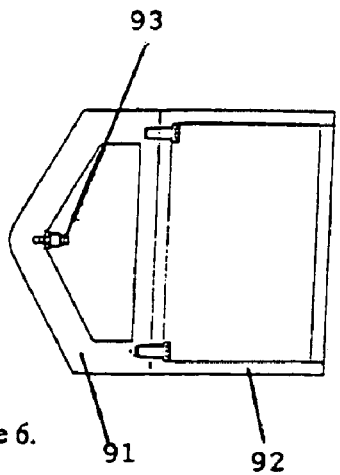
Figure 7:
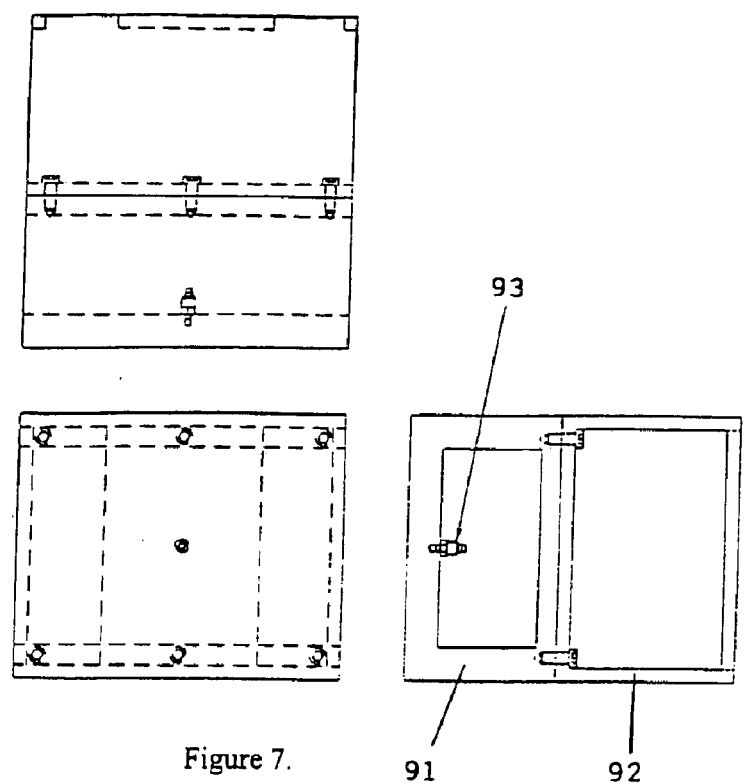
FIG. 7 illustrates the details of the strikers and accelerometer mounting location for cubical type striker.
Figure 8:
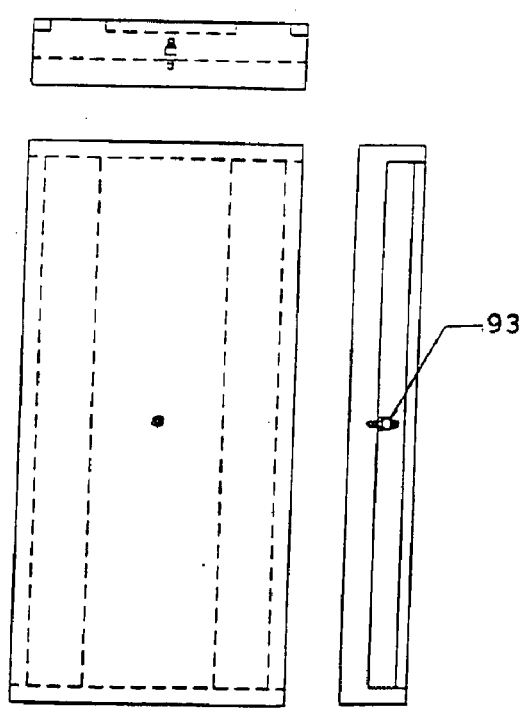
FIG. 8 illustrates the details of the strikers and accelerometer mounting location for thick plate type striker.

The lower end of the pendulum arm (48) is a portion where the striker (50) is attached to. In the preferred embodiment of the invention, striker (50) is not permanently attached to the pendulum arm (48) but is releasably fastened to the flange of the pendulum arm (48) via fastening means, for instance set screws. It is mounted preferably in such a way as to facilitate removal for replacement and also for ease of exchanging different designs of striker (50) if necessary. Also, a series of screw holes (66) is drilled along the end portion of the pendulum arm (48) to allow a range of different mounting locations for striker (50) as shown in FIG. 4. In one preferred example of the test rig, four types of striker head, each having different designs of contact geometry for impact with test item are used, namely triangular, hemispherical, cubical and thick plate type. These are clearly shown in FIGS. 5 to 8 respectively. Preferably, the striker should be made of steel or ductile iron for high wear resistance and impact strength. The striker (50) has also to be made hollow instead of solid so as to minimize its weight for facilitating the detachment and installation work during exchanging of striker (50). The striker (50) is preferably constructed of two separatable parts, that is, a striker base (91) which is attached to the pendulum arm (48) and striker head (92) which is attached to the striker base (91). Such design is also to facilitate the handling of the striker (50) during removal and mounting.

A series of masses (68) are detachably added to the pendulum arm (48) by slotting them into a pair of supporting bars (70, 72) as shown in FIGS. 2 and 3 to allow for higher impact energy if necessary. These masses (68) are preferably made from high rust resistance for long usage life and high density so that their sizes are minimized, such as steel. The supporting bars (70, 72) are threaded so that nuts can be used to securely clamp the masses (68) to the web of the pendulum arm (48).

A test item holding fixture can be any of device that can support the test item in predetermined location and orientation relative to the striker (50) prior to impact, provided that the device having sufficient stiffness and rigidity that will not deflect significantly during impact. In one preferred example of impact test on motorcycle front wheel-tyre assemblies, a wheel holding fixture (74) constituted of a pair of trapezoidal plates (76, 78) has been used. Each plate is being securely welded separately to an individual secondary base (80, 82). Both of these secondary bases (80, 82) are then bolted to a thick common base (84), which in turn bolted to the test rig's bedplate (12). Both of the secondary bases (80, 82) are laterally adjustable. Additionally, with laterally flexible, it is possible to maximize the clearance between the wheel and the holding fixture (74) so that the interference with free deformation or restriction of the distortion of the wheel structure would not occur. The common base (84) is also allowed to be adjusted in a direction perpendicular to motion of the secondary base. Both of the adjustable secondary and the common bases enable the fine-tuning of the positioning of striker (50) center relative to wheel center.

Any variety of instrumentation system can be used as data acquisition system. The preferred system for present invention is computer-based data acquisition system. For one preferred example, National Instruments PCI-6023E low cost multifunction card has been used along with the LabVIEW application software to acquire high frequency dynamic signals.

Preferably, piezoelectric transducers are selected as sensing elements for their accurate dynamic measurements and shock resistance capability. The mounting of the tranducer is preferably in such a way that it does not interfere with tranducer performance. In one preferred example for the present invention, the specific acceleration transducer employed is Kistler 8742A20 Piezotron low impedance, voltage mode single-axis shock accelerometer (93) and it is stud mounted within the wall of the striker as clearly shown in FIGS. 5 to 8.

Any appropriate image acquisition system can be employed for capturing the still and clear picture of the test item dynamic profile during impact phase such as stand alone high speed camera system, PC-based image acquisition system or integrated image acquisition system. Preferably, an imaging technique that is capable of capturing images at least at a rate of 400 frames per second is selected. In one preferred example, a stand alone high speed camera Redlake Motion Meter1000 with 1000 frame-per-second capturing capability is employed.

Any appropriate impact velocity measurements can be used to determine the striker impact velocity, such as digital rotary encoder. Preferably, a light beam emitter-detector velocity measurement system can be employed for high accuracy where the pendulum arm, when dropped, passes between the emitter and detector, generating a series of on/off pulses that can be converted into velocity by the data acquisition system. In one preferred example, two SUNX FX-13 optical sensors are used.

As a general guideline, the normal method of operating the test rig of this invention is presented as follows, taking one preferred application example of impact tests on motorcycle front wheel-tyre assemblies. The complete wheel-tyre assembly is firstly located on the specially designed wheel holding fixture that accommodate with the present invention. The striker (50) is then secured to the pendulum arm (48). By letting the pendulum hangs in its free position in which the striker (50) barely touching the surface of the tyre, the wheel holding fixture (74) is tranversely and laterally adjusted so that the impact will occur at a predetermined location and orientation. Clear all the items in the vicinity of working space to prevent injury to personnel and to reduce potential damage to any testing facility. The pulley is then operated via the chain to raise the pendulum from its rest position to the predetermined height. When the pendulum is in the ready position, the clutch coupling resists the pendulum from swinging downwardly. When everything is ready, the clutch coupling is manually actuated to disengage the pendulum mounted shaft from drive shaft to allow acceleration of the striker toward the wheel-tyre assembly. As the pendulum swings crossing the light beam of optical emitter-detector sensors, the data acquisition system will be triggered. Once the striker impact with the wheel-tyre assembly, the resultant impact response can be acquired from the output of the accelerometer. Acceleration and deceleration data is then gathered from the accelerometer mounted within the striker whilst the deformation progress of wheel-tyre assembly is captured by high speed camera for analysis and presentation.

The scope of the invention should be defined only in accordance with the claims that follow. In the following claims, reference characters used to designate claim steps are provided for convenience of description only, and are not intended to imply any particular order for performing the steps.

What is claimed is:

1. A pendulum impact test rig for conducting crash and impact experiments, comprising:
    a supporting structure attached on either a base or on the solid ground;
    a pendulum arm attached to said supporting structure wherein said pendulum arm is capable of providing a controllable center of percussion within a certain range;
    a holding fixture mounted to said base or solid ground with a fastener at a suitable location for holding a specimen to be tested;
    a striker releasably attached to said pendulum arm by an attachment means for impacting said specimen for different impact configuration; and
    a weight changeably attached to said pendulum arm by attachment means for accommodating different impact energy required; wherein said pendulum arm further comprising two inclined frame members which are attached at one of their end to both left and right sides of said pendulum arm whilst the other end are attached with an attachment means to said shaft by attachment means and plurality of fixed masses are securely attached to the end of said pendulum arm by attachment means.

2. The pendulum impact test rig for conducting crash and impact experiments as claimed in claim 1, wherein said supporting structure comprises of a pair of "A" structure supporting frames, constituted of: 4 inclined upstanding structural frame members; one horizontal main frame member secured to the vertex of said upstanding structural frame members; two horizontal structural frame members which are secured to and extend between said horizontal main frame members respectively; and a plurality of small plates attached with an attachment means at the bottom of said main frame members which are used to secure said supporting structure to the said base with an attachment means.

3. The pendulum impact test rig for conducting crash and impact experiments as claimed in claim 2, wherein said horizontal main frame member further comprising a mounting means for mounting a pair of brackets that hold a shaft of said pendulum arm and a housing for a means of bearing for both ends of said shaft are fitted into with any fitting means.

4. The pendulum impact test rig for conducting crash and impact experiments as claimed claim 1, wherein said plurality of fixed masses are fabricated from high density materials and comprises of a steel box filled with lead.

5. The pendulum impact test rig for conducting crash and impact experiments as claimed in claim 1, wherein said pendulum arm is T-shape in cross-sectional view.

6. The pendulum impact test rig for conducting crash and impact experiments as claimed in claim 1, wherein said shaft is driven by a reversible driving means through a clutch coupling means to aid in hoisting and quick releasing mechanism of the pendulum arm, where said reversible driving means is connected to a pulley means via a mechanical or electrical driving means.

7. The pendulum impact test rig for conducting crash and impact experiments as claimed in claim 1, wherein said striker is fastened to the flange of the pendulum arm via a fastening means and said striker is mounted preferably in such a way as to facilitate removal for replacement and also for ease of exchanging different designs of striker.

8. The pendulum impact test rig for conducting crash and impact experiments as claimed in claim 7, wherein said pendulum arm comprises of a plurality of holes, drilled a long the end portion of said pendulum arm to allow a range of different mounting locations for the striker.

9. The pendulum impact test rig for conducting crash and impact experiments as claimed in claim 1, wherein said striker formed of steel which is made of high wear and impact resistant material.

10. The pendulum impact test rig for conducting crash and impact experiments as claimed in claim 9, wherein said striker is made hollow instead of solid.

11. The pendulum impact test rig for conducting crash and impact experiments as claimed in claim 1, wherein said striker further comprising a striker base, which is attached to the said pendulum arm; and a striker head, which is attached with an attachment means to said striker base.

12. The pendulum impact test rig for conducting crash and impact experiments as claimed in claim 11, wherein said striker head can be of different shape depending on the impact and experimental requirement.

13. The pendulum impact test rig for conducting crash and impact experiments as claimed in claim 1, wherein said attachment means of said weights is effective with a pair of supporting bars where said weights are changeably added through slotting, and further secured with a securing means.

14. The pendulum impact test rig for conducting crash and impact experiments as claimed in claim 13, wherein said weights are made from high rust resistance and high density material.

15. The pendulum impact test rig for conducting crash and impact experiments as claimed in claim 1, wherein said holding fixture specially design to conduct impact test on motorcycle front wheel-tyre assemblies comprises of: a pair of trapezoidal plates; a laterally adjustable secondary bases, where each said trapezoidal plate is being attached with an attachment means; and a thick common base, where both of said secondary bases are then attached to with an attachment means, and in turn attached to the base or the ground.

16. The pendulum impact test rig for conducting crash and impact experiments as claimed in claim 15, wherein said common base is adjustable in a direction perpendicular to motion of the secondary bases.

17. The pendulum impact test rig for conducting crash and impact experiments as claimed in claim 1, wherein said pendulum impact test rig is further equipped with a fast speed photo capturing means to capture deformation images; a measuring means to capture impact velocity history; an electronic means to trigger data acquisition; a mechanical or electrical driven means to raise the pendulum arm to required height; and a mechanical or electrical releasing means to release the pendulum arm.

\* \* \* \* \*